(12) United States Patent
Dvorak et al.

(10) Patent No.: US 9,788,867 B2
(45) Date of Patent: Oct. 17, 2017

(54) SPINAL CORRECTION SYSTEM AND METHOD

(71) Applicant: Warsaw Orthopedic, Inc., Warsaw, IN (US)

(72) Inventors: Marcel F. Dvorak, Vancouver (CA); Charles G. Fisher, Vancouver (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 193 days.

(21) Appl. No.: 14/072,400

(22) Filed: Nov. 5, 2013

(65) Prior Publication Data

US 2015/0127055 A1     May 7, 2015

(51) Int. Cl.
*A61B 17/88*      (2006.01)
*A61B 17/70*      (2006.01)
*A61B 17/56*      (2006.01)

(52) U.S. Cl.
CPC .... *A61B 17/7038* (2013.01); *A61B 2017/564* (2013.01)

(58) Field of Classification Search
CPC ........ A61B 2017/564; A61B 2017/565; A61B 17/7038; A61B 17/7035
USPC .............. 606/246, 264–278, 279, 300–321
See application file for complete search history.

(56) References Cited

U.S. PATENT DOCUMENTS

| 5,649,926 A | 7/1997 | Howland |
| 7,655,008 B2 | 2/2010 | Lenke |
| 7,794,464 B2 | 9/2010 | Bridwell |
| 8,043,345 B2 | 10/2011 | Carl |
| 8,221,474 B2 | 7/2012 | Bridwell |
| 8,277,490 B2 | 10/2012 | Freeman |
| 2007/0213715 A1 | 9/2007 | Bridwell |
| 2011/0172714 A1 | 7/2011 | Boachie-Adjei |
| 2011/0257690 A1* | 10/2011 | Rezach .............. A61B 17/7037 606/302 |
| 2013/0123851 A1* | 5/2013 | Seme ..................... A61B 17/70 606/250 |
| 2014/0100611 A1* | 4/2014 | Barry ................. A61B 17/7032 606/265 |
| 2015/0112392 A1* | 4/2015 | Anand ............... A61B 17/7011 606/279 |

* cited by examiner

*Primary Examiner* — Ellen C Hammond
*Assistant Examiner* — Christina Negrellirodrigue (57) ABSTRACT

A method for treating vertebrae comprises the steps of: connecting at least one fastener with portions of vertebrae; providing a fastener comprising a first portion including a receiver defining an implant cavity and a member disposable with the implant cavity and movable relative to the receiver, and a second portion defining a longitudinal axis and being configured to penetrate vertebral tissue, wherein the receiver is non-pivotable relative to the longitudinal axis and connecting the fastener to the vertebrae; providing a longitudinal element; connecting a first portion of the longitudinal element with the at least one fastener; derotating the vertebrae to a selected orientation; and connecting a second portion of the longitudinal element with the fastener to substantially maintain the vertebrae in the selected orientation. Systems are disclosed.

18 Claims, 7 Drawing Sheets

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury, aging and congenital abnormalities. Spinal disorders typically result in symptoms including deformity, musculoskeletal pain, neurological pain or impairment, and partial or complete loss of mobility.

Non-surgical treatments, such as medication, rehabilitation and exercise can be effective, however, may fail to relieve the symptoms associated with these disorders and prevent progression. Surgical treatment of these spinal disorders includes deformity correction, fusion, fixation, discectomy, laminectomy and implantable prosthetics. Corrective treatments may employ implants that are manipulated for engagement with vertebrae to position and realign one or more vertebrae. This disclosure describes an improvement over these prior art technologies.

SUMMARY

Accordingly, a system and method for treating vertebrae is provided. The method comprises the steps of: providing at least one first fastener and at least one second fastener; connecting the at least one first fastener with a first portion of vertebrae; connecting the at least one second fastener with a second portion of the vertebrae spaced apart from the first portion of the vertebrae; providing at least one third fastener, the at least one third fastener comprising: a first portion including a receiver defining an implant cavity and a member disposable with the implant cavity and movable relative to the receiver, and a second portion defining a longitudinal axis and being configured to penetrate vertebral tissue, wherein the receiver is non-pivotable relative to the longitudinal axis; connecting the at least one third fastener to a third portion of the vertebrae disposed between the first portion of the vertebrae and the second portion of the vertebrae; providing a longitudinal element; connecting a first portion of the longitudinal element with the at least one first fastener; segmentally derotating the vertebra to a selected orientation; and connecting a second portion of the longitudinal element with the at least one third fastener to substantially maintain the vertebra in the selected orientation.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the spinal correction system and related methods of use disclosed are discussed in terms of medical devices for the treatment of musculoskeletal disorders and more particularly, in terms of a spinal correction system and method that facilitates connection of at least one implant with vertebrae to position and align one or more vertebrae for treatment of a spine condition. In some embodiments, the spinal correction system can include instruments such as extenders, reducers and translators, which can be used to introduce a vertebral construct such as a rod to a bone fastener, such as a bone anchor or bone screw. For example, an instrument can include an extender having bone anchor attachment features on one or both sides of the instrument. In some embodiments, the extender may be used with or include a reducer assembly to introduce a spinal rod into a bone fastener.

In one embodiment, the system is employed with a method for deformity correction, such as, for example, correction of a right thoracic adolescent idiopathic scoliosis using a hybrid construct of implants including fasteners, such as, for example, multi-axial pedicle screws, sagittally adjusting screws, and manipulating the implants using implant supports, such as, for example, reduction instruments. In one embodiment, the system is employed with a method for deformity correction, such as, for example, correction of a left lumbar scoliosis. In some embodiments, the system is employed with a method and controlled sequence to efficiently and safely correct various deformity pathologies in sagittal, coronal and axial planes of vertebrae while minimizing stress on bone/screw interfaces by using sagittally adjusting screws and reduction instruments.

In one embodiment, the system is employed with a method for scoliosis correction, which includes insertion of screws with vertebrae. For example, multi-axial screws are attached with vertebrae at a T4 vertebra, a T5 vertebra, a T12 vertebra and a L1 vertebra, and sagittal angulation screws are attached with vertebrae at a T6 vertebra, a T7 vertebra, a T8 vertebra, a T9 vertebra, a T10 vertebra and a T11 vertebra. Instrument reducers are applied to the sagittal angulation screws attached with the T8-T11 vertebrae on a concave side of the T8-T11 vertebrae. A spinal rod having a concave configuration is provisionally inserted into the multi-axial screws attached with the L1 vertebra and the T12 vertebra. Without locking the spinal rod with the multi-axial screws attached with the T12 vertebra or the L1 vertebra, the spinal rod is rotated against an open surface of the instrument reducers to a selected sagittal and coronal rod position relative to the vertebrae. The spinal rod is locked with the multi-axial screws attached with the L1 vertebra and the T12 vertebra.

The scoliosis method then includes applying instrument reducers to the sagittal angulation screws attached with the T10 vertebra, the T11 vertebra and the locked multi-axial screws attached with the T12 vertebra on contiguous vertebrae, bilaterally, for example, using six instrument reducers. A single derotator is connected with the instrument reducers on the T12 vertebra, the derotator having a handle extending to the concave side of the T12 vertebra. A single derotator is connected with the instrument reducers on the T10 vertebra, the derotator having a handle extending to the convex side of the T10 vertebra. The vertebrae is segmentally derotated by manipulating the derotator connected to the T12 vertebra and applying a force in a first direction to the T12 vertebra, for example, by holding the T12 vertebra neutral and manipulating the derotator connected to the T10 vertebra and applying a force in a second direction to the T10 vertebra, for example, derotating the T10 vertebra in the second direction.

The scoliosis method then includes manipulating the threaded components of the reduction instruments to pull the sagittal angulation screws attached with the T10 vertebra and the T11 vertebra up into the spinal rod while maintaining and fine tuning derotation. The rod is then provisionally locked to the sagittal angulation screws with the set screw. In some embodiments, the scoliosis method includes repeating the derotation method steps for the T9 and T11 vertebrae. In some embodiments, the scoliosis method includes repeating the derotation method steps for vertebrae of the lumbar, cervical, thoracic and pelvic regions of a spinal column.

In some embodiments, the vertebrae can be distracted in a concave orientation and/or for angular sagittal plane correction for increasing kyphosis using the instrument reducers as a lever prior to final tightening of set screws with the fasteners. For example, this distraction can be performed initially at the apex of the disorder and then cephalad and caudal from a mid-portion of the spinal rod. In some embodiments, the sagittal angulation screws facilitate kyphosis through concave distraction on a pre-curved kyphosis spinal rod. In some embodiments the sagittal angulation screws can be directly manipulated to increase kyphosis by tilting the instrument reducers away from the apex. In some embodiments, the convex side of the vertebrae can be distracted by initially distracting at the apex of the disorder and compressing to the apex while tilting the instrument reducers away from the apex to facilitate kyphosis. Such distraction can be performed after segmental derotation and/or prior to final tightening and/or in situ rod bending.

In some embodiments, the system is employed for axial derotation of vertebral bodies to improve chest wall volume and pulmonary function. In one embodiment, the system includes pedicle screws placed in the vertebral bodies that provide anchors for spinal manipulation. In one embodiment, the system includes implant supports, such as, for example, reduction instruments attached to the pedicle screws that are configured as derotation levers and are linked together to distribute derotation forces applied to components of the system. In one embodiment, the system is configured for linking two reduction instruments across a single vertebral body in a segmental configuration. In one embodiment, the system includes a segmental link. The segmental link is configured for disposal of concave and convex implant supports. In one embodiment, the link includes a tightening/derotation handle.

In some embodiments, the spinal correction system may include instruments that are connected or attached to an instrument(s) such as, for example, a lateral translation handle or derotation instruments. In one embodiment, one or all of the components of the surgical system are disposable, peel-pack, pre-packed sterile devices used with a spinal correction system. One or all of the components of the spinal correction system may be reusable. The spinal correction system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of a surgical system, such as, for example, a spinal correction system 10 in accordance with the principles of the present disclosure.

The components of spinal correction system 10 can be fabricated from biologically acceptable materials suitable for medical applications, including metals, synthetic polymers, ceramics and bone material and/or their composites, depending on the particular application and/or preference of a medical practitioner. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations. Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with an open or mini-open, minimal access and/or minimally invasive including percutaneous surgical technique for engagement with an implant, such as, for example, a bone fastener for a correction treatment at a surgical site within a body of a patient, for example, a section of a spine to treat various spine pathologies, such as, for example, adolescent idiopathic scoliosis and Scheuermann's kyphosis. In one embodiment, the components of spinal correction system 10 are configured to deliver and introduce an implant, such as, for example, a vertebral construct such as a rod to a bone fastener.

Figure 1:
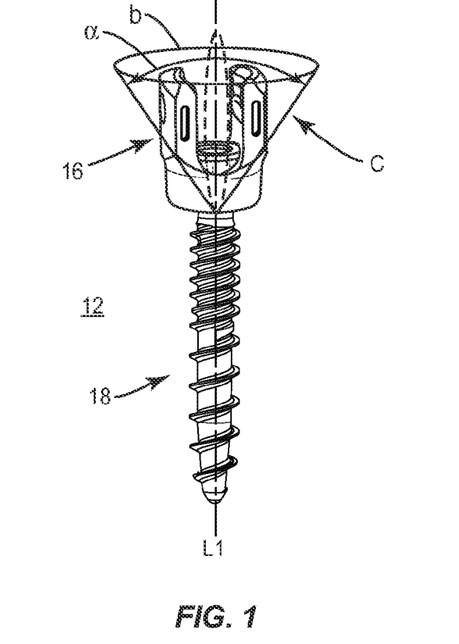
FIG. 1 is a perspective view of components of one embodiment of a system in accordance with the principles of the present disclosure.
Figure 3:
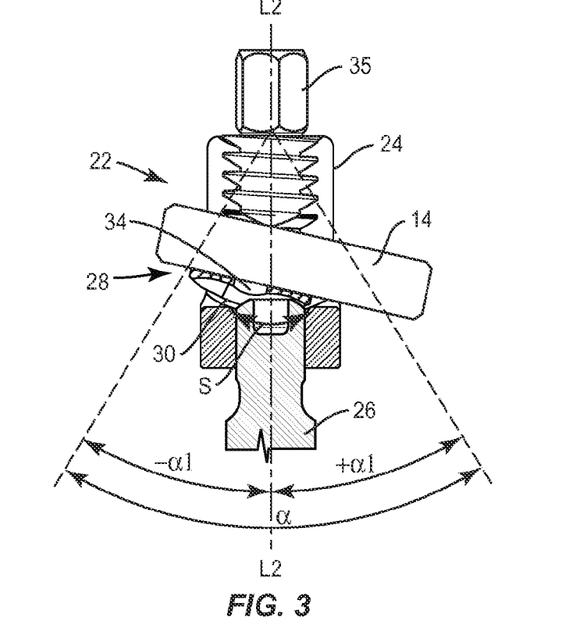
FIG. 3 is a break away cross section view of the components shown in FIG. 2.
Figure 9:
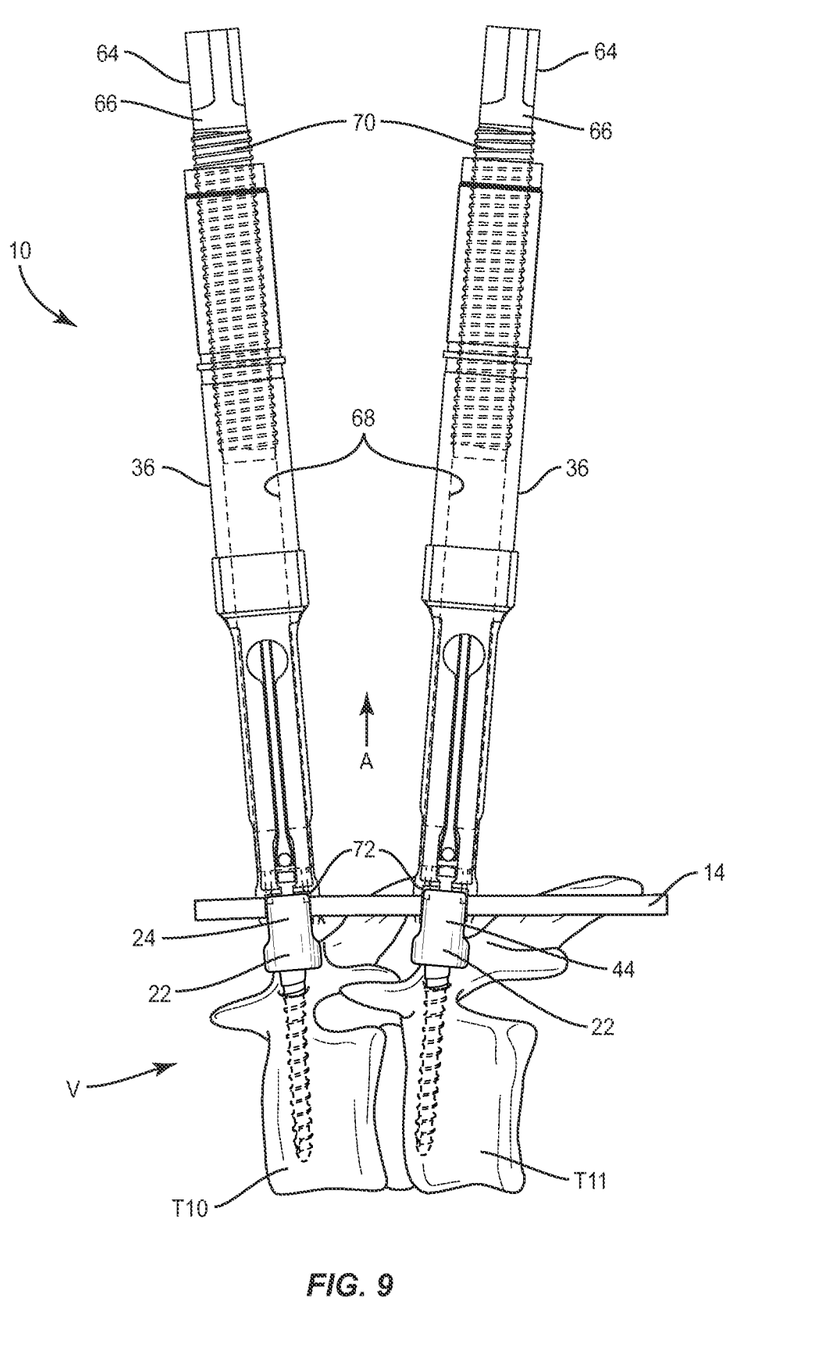
FIG. 9 is a break away side view of the components and vertebrae shown in FIG. 6.

Spinal correction system 10 includes a fastener, such as, for example, a multi axial bone screw (MAS) 12, as shown in FIG. 1, that connects a longitudinal element, such as, for example, a spinal rod 14, as shown in FIGS. 3 and 9, to tissue, such as, for example, vertebrae and/or components of system 10, such as, for example, connectors, plates and other constructs, as will be described, MAS 12 defines a longitudinal axis L1. MAS 12 comprises a first portion, such as, for example, a receiver 16 and a second portion, such as, for example, an elongated shaft 18 configured for penetrating tissue.

Shaft 18 has a cylindrical cross section configuration and includes an outer surface having an external thread form. In some embodiments, the external thread form may include a single thread turn or a plurality of discrete threads. In some embodiments, other engaging structures may be located on shaft 18, such as, for example, a nail configuration, barbs, expanding elements, raised elements and/or spikes to facilitate engagement of shaft 18 with tissue, such as, for example, vertebrae.

In some embodiments, all or only a portion of shaft 18 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 18 may include one or a plurality of openings. In some embodiments, all or only a portion of the outer surface of shaft 18 may have alternate surface configurations to enhance fixation with tissue such as, for example, rough, arcuate, undulating, mesh, porous, semi-porous, dimpled and/or textured according to the requirements of a particular application. In some embodiments, all or only a portion of shaft 18 may be disposed at alternate orientations, relative to the longitudinal axis, such as, for example, transverse, perpendicular and/or other angular orientations such as acute or obtuse, co-axial and/or may be offset or staggered. In some embodiments, all or only a portion of shaft 18 may be cannulated.

Receiver 16 includes a pair of spaced apart arms having an inner surface that defines a U-shaped passageway. The passageway is configured for disposal of an implant, such as, for example, spinal rod 14. In some embodiments, all or only a portion of the passageway may have alternate cross section configurations, such as, for example, oval, oblong, triangular, square, polygonal, irregular, uniform, non-uniform, offset, staggered, and/or tapered. In some embodiments, the arms of receiver 16 may be disposed at alternate orientations, relative to the longitudinal axis, such as, for example, transverse, perpendicular and/or other angular orientations such as acute or obtuse, co-axial and/or may be offset or staggered.

Figure 4:
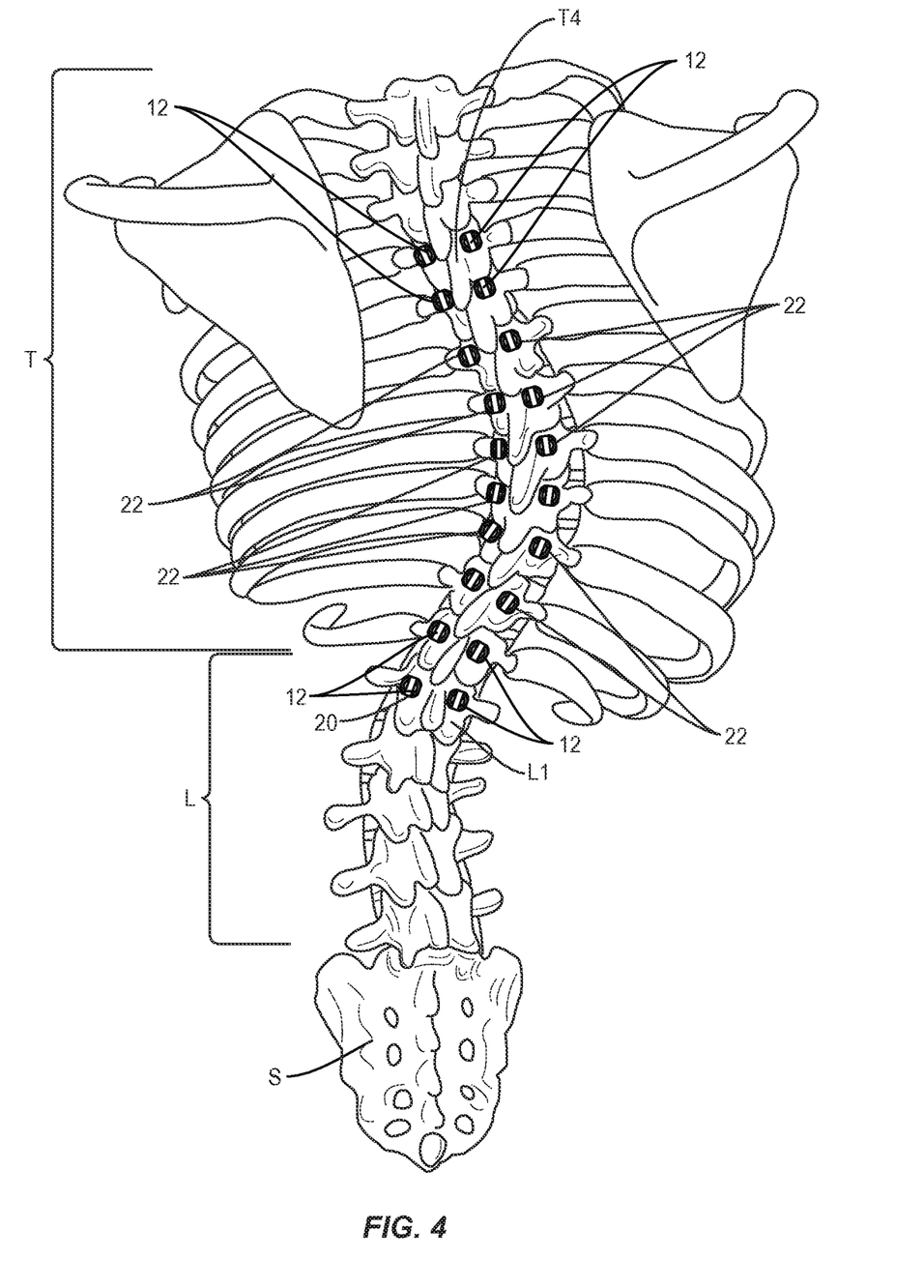
FIG. 4 is a perspective view of components of one embodiment of a system in accordance with the principles of the present disclosure disposed with vertebrae.

In one embodiment, as shown in FIG. 1, MAS 12 has a multi axial configuration such that receiver 16 is rotatable to a selected angle through and within an angular range α relative to axis L1 in a plurality of planes that lie in a cone configuration C. The area and/or volume defined by cone C, which includes the configuration disposed between axis L1 and a circular base b, is defined by the range of motion of receiver 16 about axis L1. The plurality of planes includes a locus of all straight line segments that join axis L1 and base b. For example, receiver 16 is separately rotatable to a selected angle within angular range α in each plane corresponding to a particular straight line segment that lies in cone configuration C. The inner surface of receiver 16 includes a thread form configured for engagement with a coupling member, such as, for example, a set screw 20, as shown in FIG. 4. Set screw 20 is threaded with receiver 16 to attach, provisionally fix and/or lock spinal rod 14 with MAS 12, as described.

Figure 2:
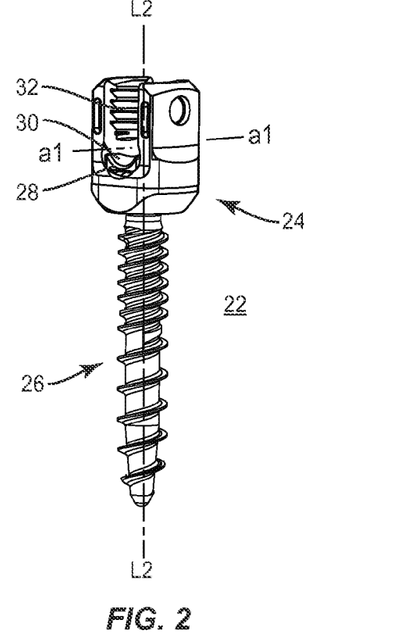
FIG. 2 is a perspective view of components of one embodiment of a system in accordance with the principles of the present disclosure.

Spinal correction system 10 includes a fastener, such as, for example, a sagittal angulation screw (SAS) 22, as shown in FIGS. 2 and 3, which connects a longitudinal element, such as, for example, spinal rod 14 to tissue, such as, for example, vertebrae and/or components of system 10, such as those described. SAS 22 comprises a first portion, such as, for example, a receiver 24 and a second portion, such as, for example, an elongated shaft 26 configured for penetrating tissue, similar to shaft 18 described.

Receiver 24 includes a pair of spaced apart arms having an inner surface that defines a U-shaped passageway, similar to receiver 16 described. The inner surface of receiver 24 is configured to receive at least a portion of a pivoting member, such as, for example, a saddle 28 for engagement with receiver 24. Receiver 24 is fixed and nonpivotable relative to shaft 26, which defines a longitudinal axis L2. In some embodiments, receiver 24 is rotatable relative to shaft 26.

Saddle 28 defines a surface that is curved and configured for slidable engagement with the inner surface of receiver 24 along an arcuate path S, as shown in FIG. 3. Saddle 28 defines a concave surface 30 that defines an implant cavity 32 with receiver 24. Implant cavity 32 defines an axis a1 transverse and movable relative to axis L2. Implant cavity 32 is configured to receive and movably support at least a portion of an implant, such as, for example, spinal rod 14 such that spinal rod 14 can translate axially relative to implant cavity 32 along axis a1 prior to fixation and is pivotable with saddle 28, as shown in FIG. 3. In some embodiments, at least a portion of the implant may be disposed within implant cavity 32 for relative movement in orientations relative to axis a1, such as, for example, transverse, perpendicular and/or other angular orientations such as acute or obtuse, co-axial and/or may be offset or staggered. In some embodiments, implant cavity 32 may have alternate cross section configurations, such as, for example, oval, oblong, triangular, rectangular, square, polygonal, irregular, uniform, non-uniform, variable and/or tapered.

Saddle 28 includes a through opening 34 extending therethrough along axis L2 and configured for alignment with a socket of shaft 26. Through opening 34 is substantially circular and defines a passageway through saddle 28 for a tool to tighten SAS 22 with vertebrae. In some embodiments, all or only a portion of through opening 34 may be variously configured and dimensioned, such as, for example, oval, oblong, triangular, square, rectangular, polygonal, irregular, uniform, non-uniform, offset, staggered, tapered, consistent or variable, depending on the requirements of a particular application.

In some embodiments, saddle 28 may be elastic and pliable in a configuration to react to forces applied and/or force changes, such as, for example, patient growth, trauma and degeneration, and/or component creep, deformation, damage and degeneration, to maintain the applied force transmitted from an implant positioned in implant cavity 32 substantially constant. In some embodiments, saddle 28 can facilitate maintenance of a holding force on an implant positioned in implant cavity 32 to maintain the holding force relatively constant despite growth and changes to SAS 22.

Saddle 28 translates relative to receiver 24 along arcuate path S such that saddle 28 is selectively rotatable relative to receiver 24 in a plane, such as, for example, a sagittal plane of a body of a patient. Saddle 28 is rotatable about axis a1 through an angular range α, as shown in FIG. 3. Saddle 28 is pivotable along arcuate path S through an angular range α at +/− an angle α1 relative to axis L2. In some embodiments, angular range α may include a range of approximately 0 to 26 degrees. In some embodiments, angle α1 may include a range of approximately +/−13 degrees. In some embodiments, saddle 28 may be disposed with receiver 24 for relative movement in orientations relative to axis a1, such as, for example, transverse, perpendicular and/or other angular orientations such as acute or obtuse, co-axial and/or may be offset or staggered. In some embodiments, saddle 28 may move relative to receiver 24 in alternate planes relative to a body, such as, for example, vertical, horizontal, diagonal, transverse, coronal and/or sagittal planes of a body. The inner surface of receiver 24 includes a thread form configured for engagement with a coupling member, such as, for example, a set screw 35. Set screw 35 is threaded with receiver 24 to attach, provisionally fix and/or lock spinal rod 14 with SAS 22, as described.

In some embodiments, spinal correction system 10 can include one or a plurality of fasteners, such as those described herein and/or fixation elements, which may be employed with a single vertebral level or a plurality of vertebral levels. In some embodiments, the fasteners may be engaged with vertebrae in various orientations, such as, for example, series, parallel, offset, staggered and/or alternate vertebral levels. In some embodiments, the fasteners and/or fixation elements may include one or a plurality of pedicle screws, mono-axial screws, uni-planar screws, fixed screws, anchors, tissue penetrating screws, conventional screws, expanding screws, wedges, anchors, buttons, dips, snaps, friction fittings, compressive fittings, expanding rivets, staples, nails, adhesives, posts, fixation plates and/or posts. These bone fasteners and/or fixation elements may be coated with an osteoinductive or osteoconductive material to enhance fixation, and/or include one or a plurality of therapeutic agents.

In some embodiments, all or only a portion of spinal rod 14 may have a semi-rigid, rigid or elastic configuration, and/or have elastic properties, such as the elastic properties corresponding to the material examples described above, such that spinal rod 14 provides a selective amount of expansion and/or extension in an axial direction. In some embodiments, spinal rod 14 has a flexible configuration, which includes movement in a lateral or side to side direction and prevents expanding and/or extension in an axial direction upon fixation with vertebrae. In some embodiments, spinal rod 14 may be compressible in an axial direction. Spinal rod 14 can include a plurality of separately attachable or connectable portions or sections, or may be monolithically formed as a single continuous element. System 10 can include one or a plurality of spinal rods. In some embodiments, spinal rod 14 is configured to extend over one or a plurality of vertebral levels.

Spinal rod 14 can have a uniform thickness/diameter. In some embodiments, spinal rod 14 may have various surface configurations, such as, for example, rough, threaded for connection with surgical instruments, arcuate, undulating, porous, semi-porous, dimpled, polished and/or textured according to the requirements of a particular application. In some embodiments, the thickness defined by spinal rod 14 may be uniformly increasing or decreasing, or have alternate diameter dimensions along its length. In some embodiments, spinal rod 14 may have various cross section configurations, such as, for example, oval, oblong, triangular, rectangular, square, polygonal, irregular, uniform, non-uniform, variable and/or tapered.

In assembly, operation and use, spinal correction system 10 is employed with a surgical procedure, such as, for example, a correction treatment to treat adolescent idiopathic scoliosis and/or Scheuermann's kyphosis of a spine. It is contemplated that one or all of the components of spinal correction system 10 can be delivered or utilized as a pre-assembled device or can be assembled in situ.

Figure 5:
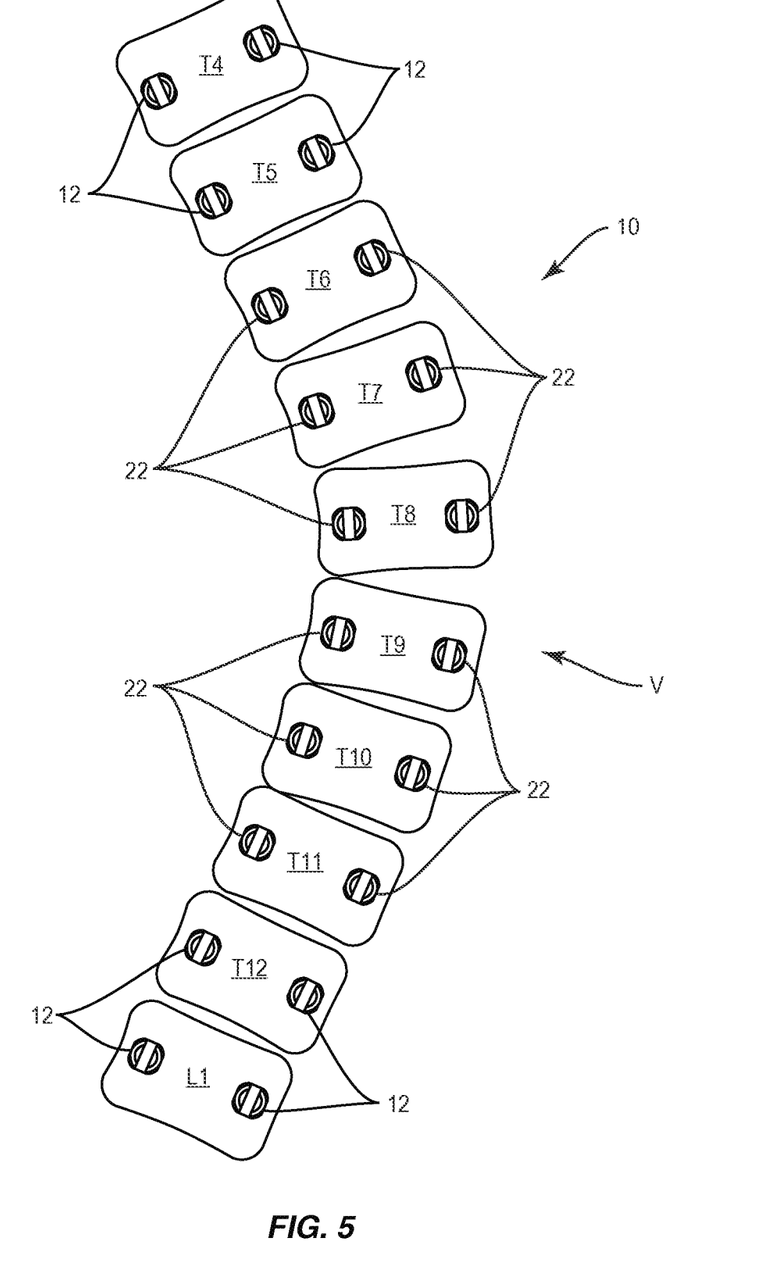
FIG. 5 is a schematic view of the components and vertebrae shown in FIG. 4.

For example, spinal correction system 10 can be employed with a surgical treatment for scoliosis correction of an affected section of a spinal column and adjacent areas within a body, such as, for example, vertebral levels, vertebra T4 (T4), vertebra T5 (T5), vertebra T6 (T6), vertebra T7 (T7), vertebra T8 (T8), vertebra T9 (T9), vertebra T10 (T10), vertebra T11 (T11), vertebra T12 (T12) and vertebra L1 (L1) of vertebrae V, as shown in FIGS. 4 and 5. In some embodiments, spinal correction system 10 may be employed with one or a plurality of vertebrae.

In use, to treat T4-L1, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

One or a plurality of incisions are made in the body of a patient and a cutting instrument (not shown) creates one or a plurality of surgical pathways and/or openings for implantation of components of spinal correction system 10. A preparation instrument (not shown) can be employed to prepare tissue surfaces of T4-L1, as well as for aspiration and irrigation of a surgical region according to the requirements of a particular surgical application.

Pilot holes (not shown) are made bilaterally in T4-L1 for receiving MAS 12 and SAS 22. The threaded shaft of each MAS 12 and SAS 22 is inserted, drilled or otherwise fixed to T4-L1. MAS 12 are attached with T4, T5, T12 and L1. SAS 22 are attached with T6, T7, T8, T9, T10 and T11.

Figure 6:
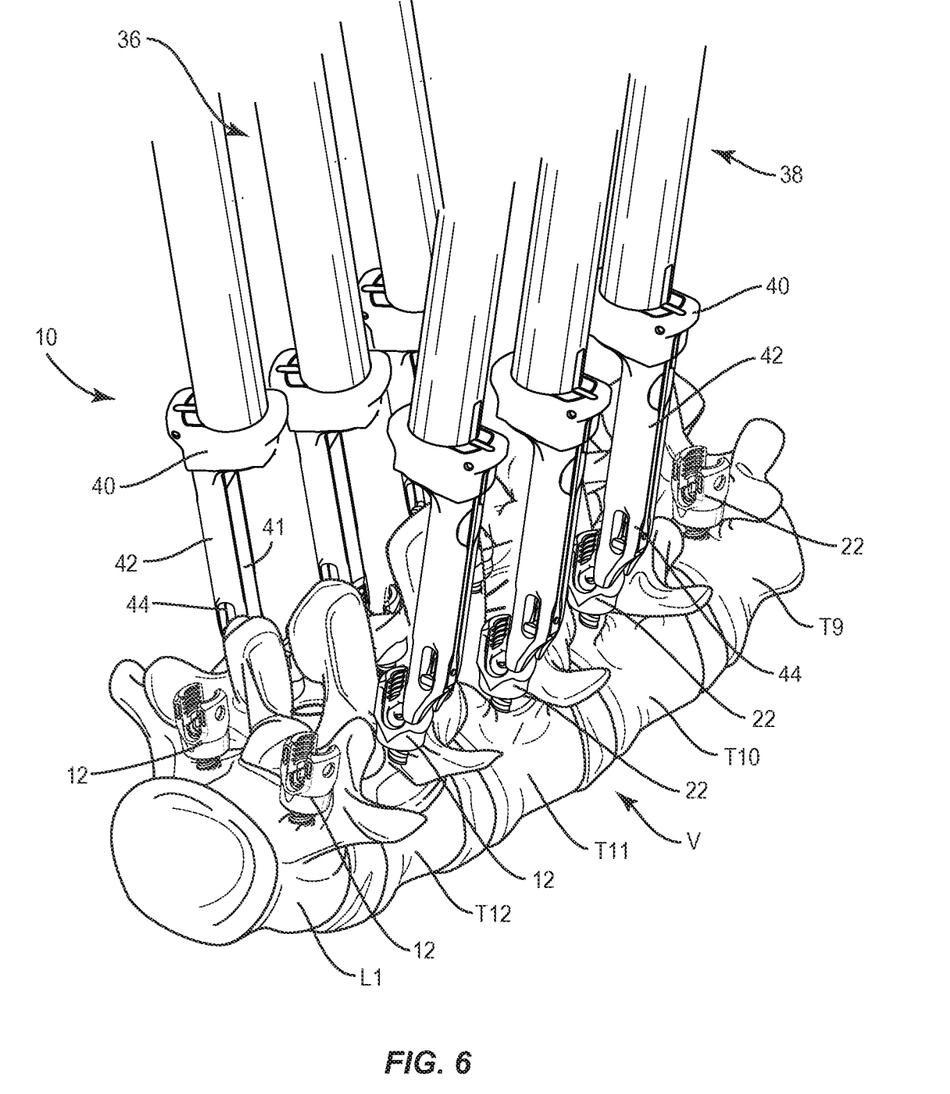
FIG. 6 is a perspective view of the components and vertebrae shown in FIG. 4 and implant supports of the system.

System 10 includes implant supports, such as, for example, extenders and/or reduction instruments 36, 38 that are applied to SAS 22 attached with T10, T11 and MAS 12 attached with T12 on contiguous vertebrae, bilaterally, for example, using six reduction instruments 36, 38, as shown in FIG. 6. Instruments 36, 38 are oriented for manipulation, alignment and capture of MAS 12 and SAS 22. Instruments 36 are configured for disposal with a concave portion of T4-L1 and instruments 38 are configured for disposal with a convex portion of T4-L1. In some embodiments, one or a plurality of instruments 36 or instruments 38 can be applied to a respective concave or convex portion of vertebrae V for performing one or a plurality of steps employing spinal correction system 10. In one embodiment, instruments 36 and/or instruments 38 are disposed in series along vertebrae V such that an instrument is disposed with each vertebral level of a treated section. In one embodiment, instruments 36 and/or instruments 38 are disposed on alternating and/or spaced apart vertebral levels of vertebrae V such that an instrument is disposed on every other vertebral level. In some embodiments, instruments 36 and/or instruments 38 may be alternated and/or spaced apart over one or a plurality of vertebral levels of a treated section of vertebrae V.

An instrument release 40 of each instrument is manipulated to move leg extensions 42 in an outward direction such that distal engagement parts 44 move outwardly and are disposed in an open position. Distal engagement parts 44 are brought into dose proximity with the receivers of each of MAS 12 and SAS 22 to provide a single sided engagement with each of MAS 12 and SAS 22. Instrument release 40 is manipulated such that leg extensions 42 are moved inwardly and distal engagement parts 44 are disposed in a closed position to capture each of MAS 12 and SAS 22 in releasable fixation.

Instruments 36 are applied to SAS 22 attached with T8-T11 on a concave side of T8-T11. Spinal rod 14 extends in a configuration for attachment with vertebrae V between T4-L1. Spinal rod 14 has a concave configuration and is inserted into and, using set screws 20, provisionally fixed with MAS 12 attached with the concave side of L1 and T12. Without locking spinal rod 14 with MAS 12 attached with L1 and T12, spinal rod 14 is rotated against an open surface 41 of leg extensions 42 of instruments 36 to a selected sagittal and coronal rod position relative to vertebrae V. In some embodiments, each of the open surfaces 41 of instruments 36, 38 can be oriented in a concave facing direction or a convex facing direction. In some embodiments, an instrument 38 is applied to one or a plurality of vertebral levels of vertebrae V to neutralize the force exerted on vertebrae V while spinal rod is rotated to facilitate manipulation of spinal rod 14 to the selected position. Spinal rod 14 is locked with MAS 12 attached with the concave side of L1 and T12 via set screws 20.

Figure 7:
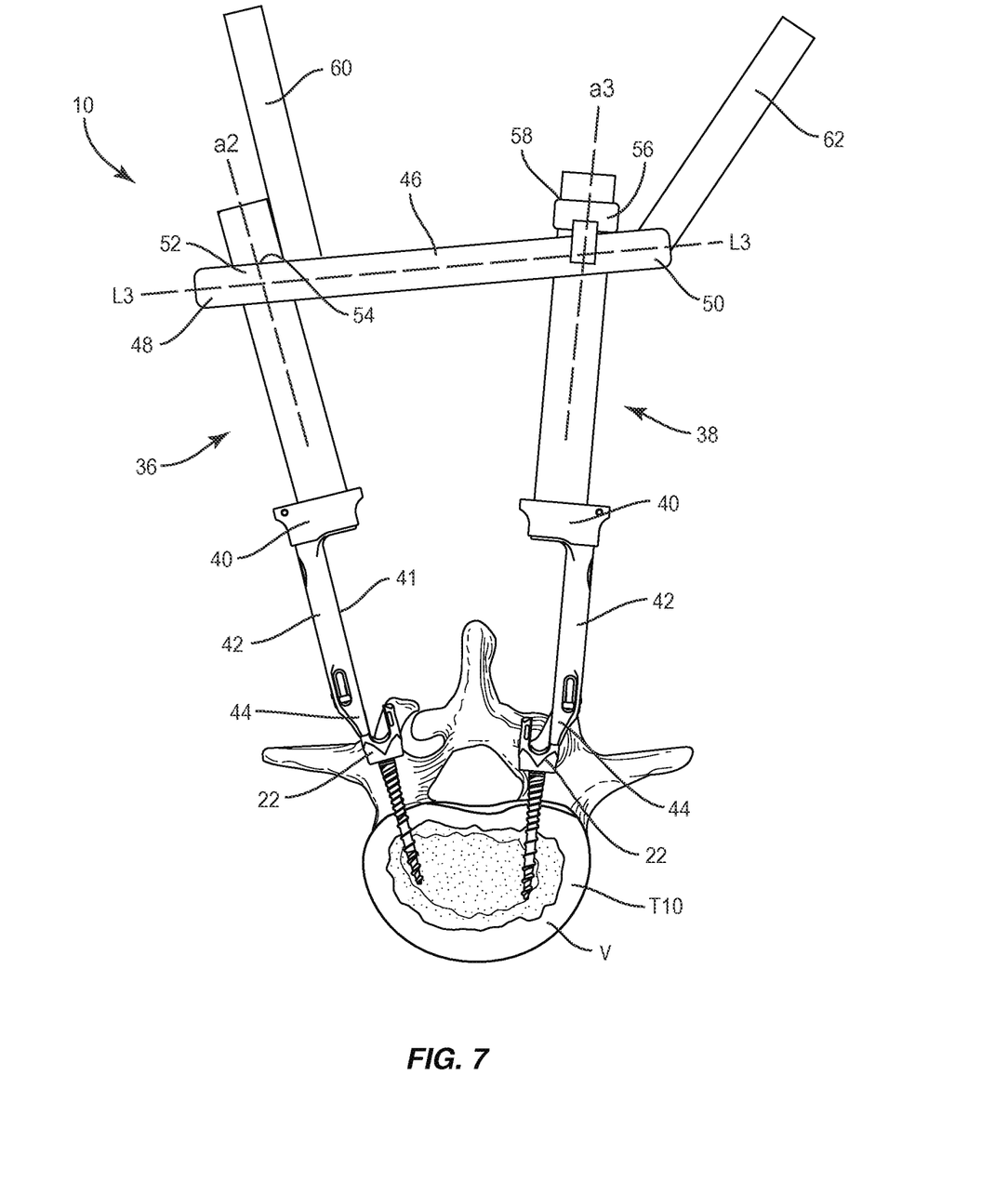
FIG. 7 is a cutaway axial view of the components and vertebrae shown in FIG. 6.
Figure 8:
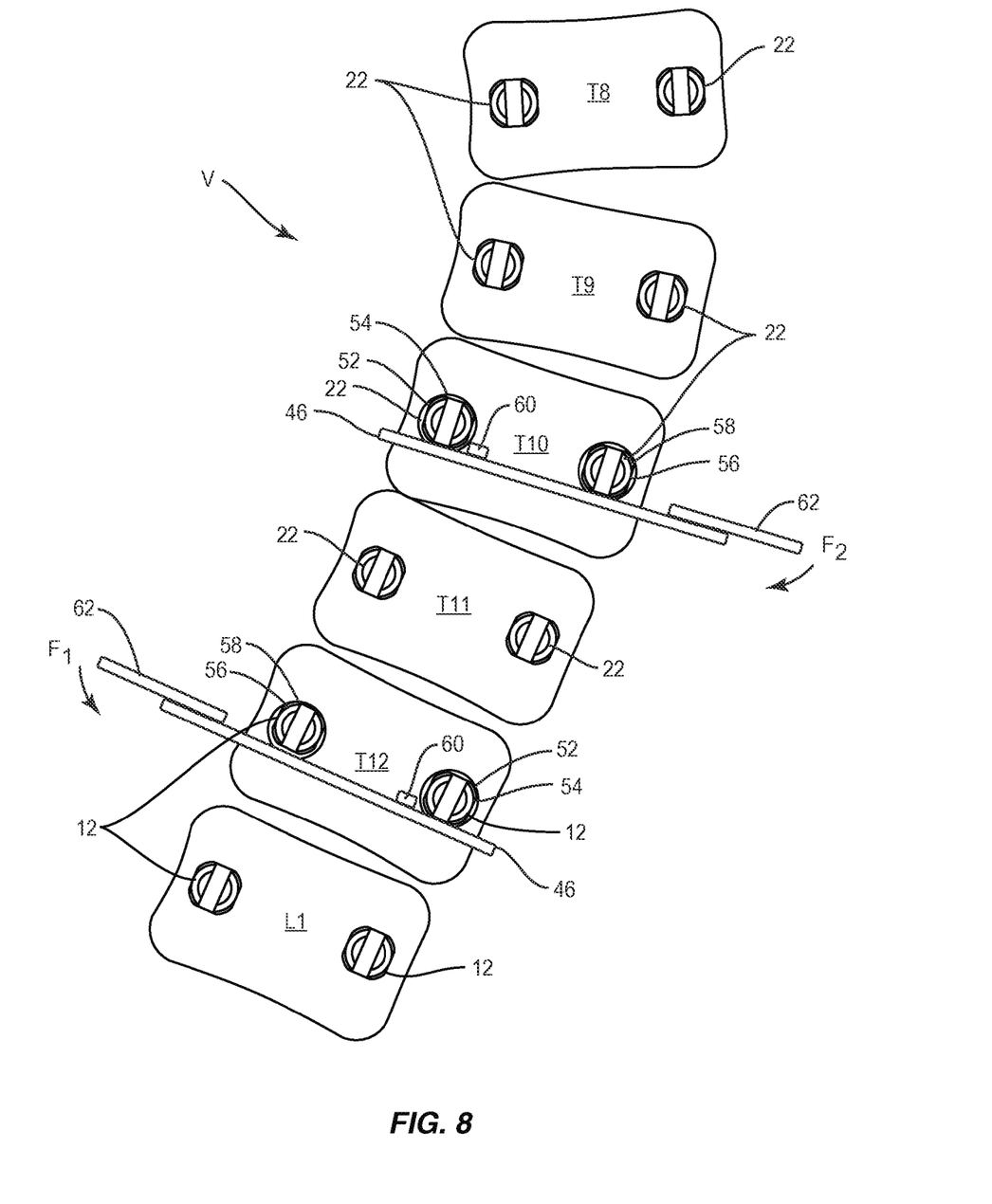
FIG. 8 is a schematic view of the components and vertebrae shown in FIG. 7.

Spinal correction system 10 includes a derotation instrument, such as, for example, a derotator 46, as shown in FIGS. 7 and 8, defining a longitudinal axis L3. Derotator 46 is configured for manipulation and resultant application of one or a plurality of forces and/or moments for application to a body to create, for example, a derotation force for a spinal treatment. Derotator 46 extends between an end 48 and an end 50. In some embodiments, system 10 may include one or a plurality of derotation instruments.

End 48 includes a collar 52 that defines an opening 54. Opening 54 defines an axis a2. Axis a2 is disposed at a transverse orientation relative to axis L3. Opening 54 is configured for disposal of a surgical instrument, such as, for example, instrument 36 and/or instrument 38. End 50 includes a collar 56 that defines an opening 58. Opening 58 defines an axis a3. Axis a3 is disposed at a transverse orientation relative to axis L3. Opening 58 is configured for disposal of a surgical instrument, such as, for example, instrument 36 and/or instrument 38.

Derotator 46 includes a dorsal handle 60 disposed intermediate ends 48, 50 and disposed perpendicular to axis L3. Derotator 46 includes a lateral handle 62 disposed adjacent end 50. Handle 62 extends laterally from derotator 46 and at an angular orientation relative to axis L3. In some embodiments, handle 60 and/or handle 62 may be disposed in alternate orientations relative to axis L3, such as, for example, transverse, perpendicular, offset and/or staggered. In some embodiments, derotator 46 may include one, both, or none of handles 60, 62.

Handles 60, 62 are configured for manipulation and application of forces thereto to create one or a plurality of forces and/or moments for application to a body to create, for example, a derotation force for a spinal treatment. In some embodiments, handle 60 and/or handle 62 can be removable for example, to reposition components of system 10 and/or modify treatment. In some embodiments, handles 60, 62 may be employed to displace, pull, twist or align vertebrae V.

A single derotator 46 is connected with instruments 36, 38 connected to MAS 12 attached with T12. Instrument 38 is disposed within opening 54 for connection to collar 52. Instrument 36 is disposed within opening 58 for connection to collar 56. Handle 62 of the derotator connected to T12 is oriented to extend to the concave side of T12.

A single derotator 46 is connected with instruments 36, 38 connected to SAS 22 attached with T10. Instrument 36 is disposed within opening 54 for connection to collar 52. Instrument 38 is disposed within opening 58 for connection to collar 56. Handle 62 of the derotator connected to T10 is oriented to extend to the convex side of T10.

Vertebrae V is segmentally derotated along T10-T12 via connection of instrumentation at T10 and T12 by manipulating derotator 46 connected to T12 and T10. A force F1 is applied to handle 62 of derotator 46 connected to T12, in the direction shown by the corresponding arrow in FIG. 8. Force F1 holds T12 neutral. A force F2 is applied to handle 62 of derotator 46 connected to T10, in the direction shown by the corresponding arrow in FIG. 8. Force F2 derotates T10 in an opposing direction. In some embodiments, force is applied to handle 60 and/or handle 62, for example, via manipulation of a practitioner during a surgical treatment, to displace, pull, twist or align vertebrae V. In some embodiments, upon completion of practitioner manipulation, one, a plurality or all of the derotators employed can be released from instruments 36, 38.

Instruments 36, 38 each include reducers 64, as shown in FIG. 9, configured to dispose spinal rod 14 with receivers 16, 24 of MAS 12, SAS 22, respectively. Each reducer 64 includes a handle 66 manipulable to align reducer 64 with an interior passageway 68 of each of instruments 36, 38. Reducer 64 has an outer surface 70 that is threaded with an inner surface of each of instruments 36, 38 that defines passageway 68. Reducer 64 is rotated to translate reducer 64 axially, in a proximal or distal direction relative to the instrument. Reducer 64 is translated such that an end surface 72 engages spinal rod 14 in a configuration to move spinal rod 14 distally to drive spinal rod 14 into receivers 16, 24.

Reducers 64 are manipulated incrementally and progressively in an iterative process to draw receivers 24 of SAS 22 attached with T10, T11 up to receive spinal rod 14, in the direction shown by arrow A in FIG. 9, while maintaining derotation, as described above. Such a process may evenly distribute forces between levels as reduction is achieved across the spinal column. Upon selective and/or desired reduction of spinal rod 14 with receivers 16, 24 of respective MAS 12, SAS 22 attached with T4-L1, set screws 20, 35 are employed to provisionally lock spinal rod 14 with SAS 22 attached with the concave side of T4-L1. In some embodiments, a second spinal rod 14 is attached with MAS 12, SAS 22 attached with the convex side of T4-L1, similar to the methods described herein.

In some embodiments, reducers 64 may reduce spinal rod 14 with various MAS 12 and/or SAS 22 incrementally, continuously to engagement with spinal rod 14 and/or to disengagement from spinal rod 14, during the various steps of the correction treatment. In some embodiments, the scoliosis correction method includes repeating the derotation method steps for T9 and T11, T10 and T8, T7 and T9, T7 and T5, T6 and T4, and/or other vertebrae pairs. In some embodiments, the scoliosis correction method includes repeating the derotation method steps for vertebrae of the lumbar, cervical, thoracic and pelvic regions of a spinal column. In one embodiment, the scoliosis correction method is employed with a correction of a right thoracic adolescent idiopathic scoliosis. In one embodiment, the scoliosis correction method is employed with a correction of a left lumbar scoliosis. Other corrections may also be achieved, such as curve corrections other than idiopathic scoliosis, either right of left, and in different regions of the spinal column.

In some embodiments, vertebrae V can be distracted in a concave orientation and/or for angular sagittal plane correction to desired kyphosis or lordosis using instruments 36, 38 as a lever prior to final tightening of set screws 20, 35 with MAS 12 and/or SAS 22. For example, this distraction can be performed initially at the apex of the disorder, such as, for example, at T10 and then cephalad and caudal from a mid-portion of spinal rod 14. In some embodiments, SAS 22 facilitate kyphosis through concave distraction on a pre-curved kyphosis spinal rod. In some embodiments the SAS can be directly manipulated to increase kyphosis by tilting the instrument reducers away from the apex In some embodiments, the convex side of vertebrae V can be distracted by initially distracting at the apex of the disorder and compressing to the apex while tilting instruments 36, 38 away from the apex to facilitate kyphosis. Such distraction can be performed after segmental derotation and/or prior to final tightening and/or in situ rod bending.

In some embodiments, the use of microsurgical and image guided technologies may be employed to access, view and repair spinal deterioration or damage, with the aid of spinal correction system 10. Upon completion of the procedure, the non-implanted components, surgical instruments and assemblies are removed and the incision is closed.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating vertebrae, the method comprising the steps of:
   providing at least one first fastener and at least one second fastener;
   connecting the at least one first fastener with a first portion of vertebrae;
   connecting the at least one second fastener with a second portion of the vertebrae spaced apart from the first portion of the vertebrae;
   providing at least one third fastener, the at least one third fastener comprising: a first portion including a receiver defining an implant cavity and a member positioned within the implant cavity and movable relative to the receiver, and a second portion defining a longitudinal axis and being configured to penetrate vertebral tissue, wherein the receiver is non-pivotable relative to the longitudinal axis;
   connecting the at least one third fastener to a third portion of the vertebrae disposed between the first portion of the vertebrae and the second portion of the vertebrae;
   providing a longitudinal element;
   connecting a first portion of the longitudinal element with the at least one first fastener;
   derotating the vertebrae to a selected orientation; and
   connecting a second portion of the longitudinal element with the at least one third fastener to substantially maintain the vertebrae in the selected orientation,
   wherein the at least one first fastener includes a multi-axial screw, the at least one second fastener includes a multi-axial screw and the at least one third fastener includes a sagittal angulation screw.

2. A method as recited in claim 1, wherein the step of connecting includes provisionally attaching the first portion of the longitudinal element with the at least one first fastener and further comprising a step of manipulating the longitudinal element to a selected position relative to the vertebrae.

3. A method as recited in claim 2, further comprising a step of locking the first portion of the longitudinal element with the at least one first fastener.

4. A method as recited in claim 2, wherein the step of manipulating the longitudinal element includes rotating the longitudinal element to a selected sagittal and coronal position relative to the vertebrae.

5. A method as recited in claim 2, further comprising the step of providing at least one implant support attached to the at least one third fastener and the step of manipulating the longitudinal element includes rotating the longitudinal element into engagement with the at least one implant support to a selected sagittal and coronal position relative to the vertebrae.

6. A method as recited in claim 1, wherein the step of derotating includes derotating the vertebra segmentally.

7. A method as recited in claim 1, wherein the step of derotating includes providing a first derotator and a second derotator, the first derotator being connected to a first vertebral level and extending to a concave side of the vertebrae and the second derotator being connected to a second vertebral level extending to a convex side of the vertebrae.

8. A method as recited in claim 7, wherein the step of derotating includes manipulating the first derotator to apply a force in a first direction to the first vertebral level and manipulating the second derotator to apply a force in a second direction to the second vertebral level to derotate the second vertebral level.

9. A method as recited in claim 8, wherein the step of derotating includes manipulating the first derotator to apply a force in the first direction to a third vertebral level and manipulating the second derotator to apply a force in the second direction to a fourth vertebral level to derotate the fourth vertebral level.

10. A method as recited in claim 1, wherein the step of connecting includes drawing the receiver adjacent the second portion of the longitudinal element such that the second portion of the longitudinal element engages the member to substantially maintain the vertebrae in the selected orientation.

11. A method as recited in claim 1, further comprising a step of distracting a first vertebral level relative to a second vertebral level.

12. A method for treating vertebrae, the method comprising the steps of:
   providing at least one multi-axial screw and at least one fastener;
   connecting the at least one multi-axial screw with at least one thoracic vertebral level of vertebrae; connecting the at least one fastener with at least one thoracic vertebral level and/or at least one lumbar vertebral level;
   providing at least one sagittal angulation screw;
   connecting the at least one sagittal angulation screw with at least one thoracic vertebral level;
   providing a spinal rod;
   provisionally attaching a first portion of the spinal rod with the at least one fastener;
   manipulating the spinal rod to a selected position relative to the vertebrae;
   derotating the vertebrae to a selected orientation;
   locking the first portion of the spinal rod with the at least one fastener; and
   locking a second portion of the spinal rod with the at least one sagittal angulation screw to substantially maintain the vertebrae in the selected orientation.

13. A method as recited in claim 12, wherein the step of manipulating the spinal rod includes rotating the spinal rod to a selected sagittal and coronal position relative to the vertebrae.

14. A method as recited in claim 12, further comprising the step of providing at least one implant support attached to the at least one sagittal angulation screw and the step of manipulating the spinal rod includes rotating the spinal rod into engagement with the at least one implant support to a selected sagittal and coronal position relative to the vertebrae.

15. A method as recited in claim 12, wherein the step of derotating includes providing a first derotator and a second derotator, the first derotator being connected to a first thoracic level and extending to a concave side of the vertebrae and the second derotator being connected to a second thoracic level extending to a convex side of the vertebrae.

16. A method as recited in claim 15, wherein the step of derotating includes manipulating the first derotator to apply a force in a first direction to the first thoracic level and manipulating the second derotator to apply a force in a second direction to the second thoracic level to derotate at least the second thoracic level.

17. A method as recited in claim 12, further comprising a step of distracting a first thoracic level relative to a second thoracic level.

18. A method for treating vertebrae, the method comprising the steps of:

providing a plurality of multi-axial screws and sagittal angulation screws;

attaching the multi-axial screws with each of a T4 vertebra, a T5 vertebra, a T12 vertebra and a L1 vertebra of vertebrae;

attaching the sagittal angulation screws with each of a T6 vertebra, a T7 vertebra, a T8 vertebra, a T9 vertebra, a T10 vertebra and a T11 vertebra;

providing a plurality of implant supports;

attaching the plurality of implant supports to the sagittal angulation screws at each of the T8 vertebra, the T9 vertebra, the T10 vertebra and the T11 vertebra and the multi-axial screw at the T12 vertebra;

providing a spinal rod;

provisionally attaching a first portion of the spinal rod with the multi-axial screws with each of the T12 vertebra and the L1 vertebra;

rotating the spinal rod to a selected sagittal and coronal position relative to the vertebrae;

locking the first portion of the spinal rod with the multi-axial screws at the T12 vertebra and the L1 vertebra;

providing a first derotator and a second derotator, the first rotator being connected to the implant supports attached with the T12 vertebra and extending to a concave side of the vertebrae and the second derotator being connected to the implant supports attached with the T10 vertebra and extending to a convex side of the vertebrae;

manipulating the first derotator to apply a force in a first direction to the T12 vertebra and manipulating the second derotator to apply a force in a second direction to the T10 vertebra to derotate at least the T10 vertebra; and drawing the sagittal angulation screws attached with the T10 vertebra and the T11 vertebra into engagement with the spinal rod to substantially maintain the derotation.

* * * * *

UNITED STATES PATENT AND TRADEMARK OFFICE
CERTIFICATE OF CORRECTION

PATENT NO. : 9,788,867 B2  
APPLICATION NO. : 14/072400  
DATED : October 17, 2017  
INVENTOR(S) : Dvorak et al.

Page 1 of 1

It is certified that error appears in the above-identified patent and that said Letters Patent is hereby corrected as shown below:

In the Specification

In Column 4, Line 48, delete "dearly" and insert -- clearly --, therefor.

In Column 6, Line 31, delete "described," and insert -- described. --, therefor.

In Column 7, Line 41, delete "nonpivotable" and insert -- non-pivotable --, therefor.

In Column 8, Line 52, delete "dips," and insert -- clips, --, therefor.

In Column 10, Line 25, delete "dose" and insert -- close --, therefor.

In the Claims

In Column 16, Line 4, in Claim 18, delete "rotator" and insert -- derotator --, therefor.

Signed and Sealed this  
Thirteenth Day of March, 2018

Andrei Iancu  
*Director of the United States Patent and Trademark Office*